(12) United States Patent
Gitlin

(10) Patent No.: US 8,524,768 B2
(45) Date of Patent: Sep. 3, 2013

(54) ANTIOXIDANTS FOR PREVENTING AND TREATING DISEASES CAUSED BY OXIDATIVE STRESS

(76) Inventor: Isaak Grigorievich Gitlin, Moscow (RU)

( * ) Notice: Subject to any disclaimer, the term of this patent is extended or adjusted under 35 U.S.C. 154(b) by 422 days.

(21) Appl. No.: 12/322,490

(22) Filed: Feb. 2, 2009

(65) Prior Publication Data

US 2009/0170789 A1    Jul. 2, 2009

Related U.S. Application Data

(63) Continuation-in-part of application No. PCT/RU2007/000404, filed on Jul. 27, 2007.

(30) Foreign Application Priority Data

Aug. 3, 2006   (RU) .................................. 2006128154

(51) Int. Cl.
  *A61K 31/34* (2006.01)
  *A61K 31/375* (2006.01)
  *C07D 307/62* (2006.01)

(52) U.S. Cl.
  USPC ............................................ 514/474; 436/93

(58) Field of Classification Search
  USPC ............................................ 514/474; 436/93
  See application file for complete search history.

(56) References Cited

U.S. PATENT DOCUMENTS

| | | | |
|---|---|---|---|
| 4,810,695 A | 3/1989 | Conti et al. | |
| 6,280,742 B1 | 8/2001 | Seid et al. | |
| 6,610,895 B2 | 8/2003 | Holdstock et al. | |
| 2002/0197313 A1 | 12/2002 | Richardson et al. | |
| 2004/0213829 A1 * | 10/2004 | Coleman et al. | 424/440 |

FOREIGN PATENT DOCUMENTS

| | | | |
|---|---|---|---|
| RO | 119718 B1 * | 2/2005 | |
| RU | 2281092 C2 | 8/2006 | |
| WO | WO 2008/024021 | 7/2007 | |

OTHER PUBLICATIONS de Souza et al ("Antioxidant properties of complexes of flavonoids with metal ions", Redox Report (2004), 9(2), 97-104).*
Mel'nikova et al ("Reaction of Bioflavonoids with Copper(II) Acetate in Aqueous Solution", Chemistry of Natural Compounds, vol. 38, No. 1, 2002).*
Rusin et al (Prophylaxis of iron and copper deficiency in children and adults, Gematologiya i Transfuziologiya, (1984), 29(9), pp. 39-43).*
Gao et al., "Effects of Rutin Supplementation on Antioxidant Status and Iron, Copper, and Zinc Contents in Mouse Liver and Brain", *Biol. Trace Elem. Res.* Sep. 2002; 88(3) 271-9.
Product Information—EVONIK InduStries, "EUDRAGIT® Power through Flexibility", 10 pages, accessed on Nov. 12, 2008 from http://www.pharmapolymers.com/pharmapolymers/enieudragit/ . . . .

\* cited by examiner

*Primary Examiner* — Patrick Lewis
*Assistant Examiner* — Everett White
(74) *Attorney, Agent, or Firm* — Stout, Uxa, Buyan & Mullins; Frank J. Uxa

(57) ABSTRACT

Antioxidant compositions for the treatment and prophylaxis of illnesses associated with oxidative stress and lack of oxygen in the human body, comprising a complex of a metal selected from the group consisting of iron, copper, zinc and manganese with rutin and ascorbic acid and/or dihydroascorbic acid. Methods for synthesizing the antioxidant compositions and granulates, tablets and capsules containing antioxidant compositions are also provided.

19 Claims, No Drawings

ANTIOXIDANTS FOR PREVENTING AND TREATING DISEASES CAUSED BY OXIDATIVE STRESS

CROSS-REFERENCE TO RELATED APPLICATIONS

This application is a continuation-in-part of PCT/RU2007/000404, filed Jul. 27, 2007, designating the United States, which claims priority from Russian Patent Application 2006128154 filed Aug. 3, 2006, the disclosures of each of these prior applications in their entireties being incorporated hereby by reference herein.

BACKGROUND OF THE INVENTION

The invention concerns medicine, in particular the pharmaceutical industry, namely the production of compounds that influence metabolic processes in the human body, in particular oxygenation processes.

Common to neurodegenerative diseases is progressive loss of specific nerve cells, which are associated with protein aggregation, which is caused by oxidative stress. Oxidative stress is responsible for dysfunction or death of neurons, which is the important if not the main element of the pathogenesis of the disease.

Oxidative stress is a result of unregulated formation of active oxygen forms (AOF) or reactive oxygen species (ROS) such as hydrogen peroxide, superoxide anion radical, highly active hydroxyl radical, or peroxynitrite. A high level of oxygen absorption and low antioxidant status together with insufficient ability of the organism to regenerate tissues create an elevated level of sensitivity to oxidative damage.

Peroxidation of lipids is a result of attack of radical forms of active oxygen at the double bonds of unsaturated fatty acids such as linolenic and arachidonic acids. This leads to generation of active peroxy radicals, which initiate chain reactions that include further attack at the C=C bonds of unsaturated fatty acids. Decomposition products such as 4-hydroxy-2,3-nonenal, acrolein and malondialdehyde form as a result.

An increased level of 4-hydroxy-2,3-nonenal was found in the brains of Alzheimer's patients and patients with Parkinson disease. Increased levels of acrolein and malondialdehyde derivatives were detected in the brains of Alzheimer's patients. In Parkinson's there was an increase in the level of malondialdehyde. All four DNA bases are sensitive to oxidative damage including hydroxylation, formation of carbonyl groups and nitration (changes found in the brain DNA of Alzheimer's patients.)

Increased levels of 8-hydroxyguanine and 8-hydroxy-2-deoxygyanosine (as a result of attack of hydroxyl radicals) are typical in the brains of Parkinson's patients.

Cells have their own defense mechanisms against oxidative stress, and changes seen in their activity are also good markers for oxidative stress. In the brains of patients with verified Alzheimer's disease, the activity of antioxidant proteins such as catalase, superoxide dismutase (SOD), glutathione peroxidase and glutathione reductase is increased. Oxidation of fatty acids mainly takes place in the mitochondria, and other cell compartments also contain enzymes capable of converting fatty acids to acetyl-SCoA by a pathway that is similar (but not identical) to what happens in mitochondria.

Oxidative stress (i.e., oxidation of lipids, proteins and DNA) causes damage to cell functions and formation of toxic compounds, such as peroxides, alcohols, aldehydes, ketones, cholesterol oxide. The last is toxic to lymphocytes and macrophages of blood vessels. Acrolein interrupts the reverse capture of glucose and glutamate from cell cultures, while 4-hydroxy-2,3-nonenal inhibits the neural glucose transporter, as well as the glutamate and $Na^+/K^+$-ATPase transporters. Modification of protein leads to damage to enzymes such as glutamate synthase and SOD, and oxidation of DNA lead to mutations. Disruption of intracellular calcium signaling/ROS-induced release of calcium leads to activation of glutamate receptors and, if there are other disruptions, it leads to activation of the apoptotic cascade, thus to programmed cell death.

PRIOR ART

The generation of ROS is often a result of the reaction of molecular oxygen with redox-active metals (mainly $Cu^+$ and $Fe^{2+}$), although there are also other ways, such as formation of peroxynitrite from nitrogen oxide and a superoxide radical. Currently it is considered that the chief sources of oxidative stress and production of free radicals and, correspondently Alzheimer's disease, are complexes of transitional metals with amyloid β-peptides.

All defects arising in the organism and reliably connected to the presence of active forms of oxygen have not yet been established, but there are grounds to believe that it is these forms in particular that are responsible to one degree or another for aging processes, formation of cataracts, myocardial infarcts etc.

The use of chelate complexes of chitosan with zinc, copper, iron and nickel is known (U.S. Pat. No. 6,280,742 of Aug. 28, 2001). U.S. Pat. No. 4,810,695 of Mar. 7, 1989 proposes the use of complex compounds of iron with chitosan as a chelate complex.

Currently more and more attention is paid to flavonoids (polyphenol antioxdants), in particular group P vitamins, rutin and quercetin. There is a connection between antioxidant status and complexes of rutin with iron, zinc, and copper (Biol Trance Elem Res. 2002 September; 88(3)271-9). It is well known that vitamins of group P, for example rutin, possess antioxidant properties. One of the common antioxidants is the vitamin complex "ascorutin" (ascorbic acid+rutin), which has membrane-stabilizing activity based on its ability to participate in redox processes. (M. D. Mashkovskii, Lekarstvennye sredstva [Drugs], Moscow, Novaya Volna, 2001, pp. 86-87.)

However, most of the current antioxidants have poor solubility in water and have extremely low bioavailability (ibid., p. 86).

The goal of the present invention is to develop a new antioxidant for prophylaxis and treatment of the diseases connected with oxidative stress and lack of oxygen that is capable of improving antioxidant status, increasing the partial pressure of oxygen in tissues, correcting the biological age of humans, and having excellent bioavailability, and also developing a method of producing it and a granulated form and efficient tabletting or an encapsulated preparative form.

NATURE OF THE INVENTION

Provided is an antioxidant for prophylaxis and treatment of diseases connected with oxidative stress and an insufficient amount of oxygen in the organism. The compound is a complex of a metal (iron, copper, zinc or manganese) cation with rutin and ascorbic acid and/or dehydroascorbic acid of the general formula (I):

$$Me_m Ru(AA)_r (DGAA)_p \text{-} X_n \qquad \text{(I), where}$$

Me—cation of iron, copper, zinc or manganese;
Ru—rutin
AA—ascorbic acid

DGAA—dehydroascorbic acid
X—$SO_4^{-2}$, $CH_3C(O)O^-$, or $^-OOC—CH_2—C(OH)(COO^-)—CH_2—COO^-$;
m is from 1.0 to 3;
n is from 0.7 to 9;
p/(r+p) is from 0 to 1.

In addition, an object of this invention is the development of a simple and technological method of producing an antioxidant with general formula (I), in which ascorbic acid is reacted with an alcohol solution of a metal salt, followed by treatment of the reaction mixture with rutin at a temperature from room temperature to the boiling point of the solvent. Process should be conducted at molar ratio of metal salt to ascorbic acid from 20 to 3.

If metal salts of strong acids are used, after the rutin treatment, the mixture is treated with the alkali metal salt of a weak acid in order to decrease the acidity of the product.

An object of the invention is also a granulate used to manufacture medicinal and prophylactic compounds for prophylaxis and treatment of illnesses connected with oxidative stress and lack of oxygen in the body, containing antioxidant formula (I) and, optionally, eudragit and polyvinylpyrrolidone (PVP) with the following ratio of components; wt %:

| PVP | 0-5.0, |
| eudragit | 0-11; |
| antioxidant formula (I) | remainder. |

Another object of this invention are tablets and capsules for treatment and prophylaxis of diseases connected with oxidative stress and lack of oxygen in the organism, containing antioxidant of formula (I) and optionally polyvinylpyrrolidone and eudragit and, as supplemental agents, microcrystal cellulose, calcium or magnesium stearate and talc, containing not more than 15-50% (mass) of supplemental agents.

PREFERRED EMBODIMENT OF THE INVENTION

An antioxidant, which is a complex of a metal (iron, copper, zinc or manganese) with rutin and ascorbic acid and/or dehydroascorbic acid with general formula (I) is described:

$$Me_mRu(AA)_r(DGAA)_p\text{-}X_n \quad (I), \text{ where}$$

Me—cation of iron, copper, zinc or manganese;
Ru—rutin
AA—ascorbic acid
DGAA—dehydroascorbic acid
X—$SO_4^{-2}$, $CH_3C(O)O^-$, or $^-OOC—CH_2—C(OH)(COO^-)—CH_2—COO^-$;
m is from 1.0 to 3;
n is from 0.7 to 9;
p/(r+p) is from 0 to 1.

A complex containing rutin, iron and dehydroascorbic and/or ascorbic acid is preferred:

$Fe_mRu(AA)_r(DGAA)_pX_n$, where m—number of atoms of iron with degree of oxidation 3,
m has values from 1.5 to 3,
n is from 0.7 to 9,
p/(r+p) is from 0 to 1.

Also preferred is a complex containing rutin, copper and dehydroascorbic acid and/or ascorbic acid with the general formula $Cu_mRu(AA)_r(DGAA)_pX_n$, where m takes a value from 1.0 to 3,
n is 0.7 to 6,
p/(r+p) is 0 to 1

Another complex is the one containing rutin, zinc, and dehydroascorbic and/or ascorbic acid; with the general formula:

$Zn_mRu(AA)_r(DGAA)_pX_n$, where m is from 1.0 to 3;
n is from 0.7 to 6;
p/(r+p) is from 0 to 1.

A complex containing rutin, manganese and ascorbic and/or dehydroascorbic acid is provided with the general formula $Mn_mRu(AA)_r(DGAA)_pX_n$, where m is from 1.0 to 3;
n is from 0.7 to 6;
p/(r+p) is from 0 to 1.

In the above descriptions, the complexes are disclosed as including ascorbic acid and/or dihydroascorbic acid. Therefore, the complex includes at least one of ascorbic acid and dihydroascorbic acid and in the general formula (I) and the general formula at least one of p and r is not zero.

A method for synthesis of antioxidant with general formula (I) is also described. Ascorbic acid is treated with an alcohol solution of a metal salt, then the reaction mixture is treated with rutin at a temperature from room temperature to the boiling point of the solvent. Process is conducted at molar ratio of metal salt to ascorbic acid from 20 to 3.

If metal salts of strong acids are used to decrease acidity of the product, after the rutin treatment the reaction mixture is additionally treated with the alkali metal salt of a weak acid.

In the reaction of the metal salt with ascorbic acid, partial reduction of iron from $Fe^{3+}$ to $Fe^{2+}$ and partial oxidation of ascorbic acid to dehydroascorbic acid take place. As a result, the antioxidant contains $Fe^{3+}$, $Fe^{2+}$ or $Cu^{2+}$, $Cu^{1+}$, or $Zn^{2+}$, or $Mn^{2+}$ and ascorbic acid, dehydroascorbic acid and rutin, which form a change transfer complex of formula (I).

Also described is a granulate for preparation of pharmaceutical and prophylactic means for reducing oxidative stress and treatment and prophylaxis of illnesses connected with oxidative stress and a lack of oxygen in the body, that contains an antioxidant of formula (I) and, optionally, eudragit and polyvinylpyrrolidone in the following ratio of components, wt %:

| Polyvinylpyrrolidone | 0-5.0 |
| Eudragit | 0-11 |
| Antioxidant of formula (I) | remainder. |

Also described is a tabletted or encapsulated preparative form containing said granulate and, optionally, polyvinylpyrrolidone and eudragit and, as auxiliary substances, microcrystalline wax, calcium stearate or magnesium stearate and talc, with a concentration of auxiliary substances of 15-50%.

As is well known to those in the pharmaceutical art, Eudragit® is a registered trademark of Pharma Polymers (Evonik Industries, formerly Degussa) for a variety of acrylate/methacrylic acid/methacrylates polymers and copolymers, hereinafter referred to generically as acrylic polymers useful as coatings, for example, controlled release coatings, and/or matrix materials for active ingredients. The matrix structure may be obtained by direct compression, granulation or melt techniques.

Below are examples illustrating the invention.

EXAMPLE 1

To an alcohol (ethanol) solution of trivalent iron containing (m) 3 gmol of iron (3) in the form of iron acetate (705 g) is added (r+p) 0.5 gmol of ascorbic acid (90 g), and the mixture is stirred for five minutes. With constant stirring, 1 gmol rutin (650 g) is added. Stirring is continued for 60 min. The solution is dried until homogenous powder forms. The yield is 1445 g. The iron content is 11%.

$p/(r+p)=0.3\pm0.1$
$m=3$
$n=9$
The ratio of iron (gmol)/ascorbic acid (gmol)=6
The ratio of iron (gmol)/rutin (gmol)=3

EXAMPLE 2

To an alcohol solution (isopropanol) of trivalent iron containing 1.5 gmol of iron (3) in the form of iron sulfate (603 g) is added 0.5 gmol of ascorbic acid (90 g), and the mixture is stirred while boiling for 60 min with reflux. With constant stirring, 1 gmol rutin (650 g) is added. The stirring continues for an additional 60 min. The solution is then dried until a homogeneous powder forms. Yield is 1340 g. Iron content is 6%.

$p/(r+p)=0.1\pm0.05$
$m=1.5$
$n=2.25$
Ratio of iron (gmol)/ascorbic acid (gmol)=3
Ratio of iron (gmol)/rutin (gmol)=1.5

EXAMPLE 3

To an alcohol solution (methanol) of trivalent iron containing 2 gmol iron (3) in the form of iron citrate (486 g) is added 0.5 gmol of ascorbic acid (90 g), and the solution is stirred for 30 min. With constant stirring, 1 gmol rutin (650 g) is added. Stirring is continued for 60 min. The solution is then dried until a homogenous powder is formed. Yield is 1220 g. Iron content is 8.9%.

$p/(r+p)=0.2\pm0.05$
$m=2$
$n=2$
The ratio of iron (gmol)/ascorbic acid (gmol)=4
The ratio of iron (gmol)/rutin (gmol)=2

EXAMPLE 4

To an aqueous solution of trivalent iron containing 3 gmol of iron (3) in the form of iron chloride (483 g) is added 0.5 gmol of ascorbic acid (90 g), and the mixture is stirred while boiling with reflux for 90 min. With constant stirring, 1 gmol of rutin (650 g) is added. Stirring is continued for an additional 120 min. The resulting solution is treated with sodium acetate (246 g) and the sodium chloride is filtered out. The solution is then dried until a homogeneous powder forms. Yield is 1460 g of powder. The iron content is 11%.

$p/(r+p)=0.3\pm0.1$
$m=3$
$n=9$
The ratio of iron (gmol)/ascorbic acid (gmol)=6
The ratio of iron (gmol)/rutin (gmol)=3

EXAMPLE 5

To a solution of trivalent iron containing 2 gmol of iron (3) in the form of iron chloride (322 g) is added 0.5 gmol ascorbic acid (90 g), and the mixture is boiled while stirring with reflux for 90 min. With constant stirring, 1 gmol rutin (650 g) is added. Stirring is continued for 120 min. The solution is then treated with sodium acetate (600 g) and the NaCl that forms is filtered out. The solution is dried until a homogeneous powder forms. Yield is 1660 g of powder. Iron content is 6.5%.

$p/(r+p)=0.2\pm0.05$
$m=2$
$n=6$
The ratio of iron (gmol)/ascorbic acid (gmol)=4
The ratio of iron (gmol)/rutin (gmol)=2

EXAMPLE 6

To a solution of trivalent iron containing 1.5 gmol of iron (3) in the form of iron chloride (240 g) is added 0.5 gmol ascorbic acid (90 g), and the mixture is boiled while stirring with reflux for 90 min. With constant stirring, 1 gmol rutin (650 g) is added. Stirring is continued for 120 min. The solution is then treated with sodium acetate (318 g) and the NaCl that forms is filtered out. The solution is dried until a homogeneous powder forms. Yield is 1290 g of powder. Iron content is 6.2%.

$p/(r+p)=0.1\pm0.05$
$m=1.5$
$n=1.5$
The ratio of iron (gmol)/ascorbic acid (gmol)=4
The ratio of iron (gmol)/rutin (gmol)=1.5

EXAMPLE 7

To a solution of trivalent iron containing 3 gmol of iron (3) in the form of iron chloride (483 g) is added 0.5 gmol ascorbic acid (90 g), and the mixture is boiled while stirring with reflux for 90 min. With constant stirring, 1 gmol rutin (650 g) is added. Stirring is continued for 120 min. The solution is then treated with sodium acetate (636 g) and the NaCl that forms is filtered out. The solution is dried until a homogeneous powder forms. Yield is 1850 g of powder. Iron content is 8.7%.

$p/(r+p)=0.3\pm0.1$
$m=3$
$n=3$
The ratio of iron (gmol)/ascorbic acid (gmol)=6
The ratio of iron (gmol)/rutin (gmol)=3

EXAMPLE 8

To a solution of trivalent iron containing 4.5 gmol of iron (3) in the form of iron chloride (729 g) is added 0.5 gmol ascorbic acid (90 g), and the mixture is boiled while stirring with reflux for 90 min. With constant stirring, 1 gmol rutin (650 g) is added. Stirring is continued for 120 min. The solution is then treated with sodium acetate (954 g) and the NaCl that forms is filtered out. The solution is dried until a homogeneous powder forms. Yield is 2420 g of powder. Iron content is 10%.

$p/(r+p)=0.5\pm0.1$
$m=4.5$
$n=4.5$
The ratio of iron (gmol)/ascorbic acid (gmol)=9
The ratio of iron (gmol)/rutin (gmol)=4.5

EXAMPLE 9

To an aqueous solution of trivalent iron containing 10 gmol of iron (3) in the form of iron chloride (1620 g) is added 0.5 gmol of ascorbic acid (90 g), and the mixture is stirred while boiling with reflux for 90 min. With constant stirring, 1 gmol of rutin (650 g) is added. Stirring is continued for an additional 120 min. The resulting solution is treated with sodium acetate (2220 g) and the sodium chloride that forms is filtered out. The solution is then dried until a homogeneous powder forms. Yield is 4580 g of powder. The iron content is 11.7%.

$p/(r+p)=1\pm0.1$
$m=10$
$n=1$
The ratio of iron (gmol)/ascorbic acid (gmol)=20
The ratio of iron (gmol)/rutin (gmol)=10

EXAMPLE 10

To an alcohol solution (95% ethanol) of divalent iron containing 2 gmol of iron (2) in the form of iron chloride (250 g) is added 0.5 gmol of ascorbic acid (90 g), and the mixture is stirred while boiling with reflux for 90 min. With constant stirring, 1 gmol of rutin (650 g) is added. Stirring is continued for an additional 120 min. The resulting solution is treated with sodium acetate (296 g) and the sodium chloride that forms is filtered out. The solution is then dried until a homogenous powder forms. Yield is 1286 g of powder. Iron content is 8.4%.

$p/(r+p)=0\pm0.05$
$m=2$
$n=1.33$
The ratio of iron (gmol)/ascorbic acid (gmol)=4
The ratio of iron (gmol)/rutin (gmol)=2

EXAMPLE 11

To an alcohol solution (95% ethanol) of divalent copper containing 2 gmol of copper (2) in the form of copper chloride (270 g) is added 0.5 gmol of ascorbic acid (90 g) and the mixture is stirred while boiling with reflux for 90 min. With constant stirring, 1 gmol of rutin (650 g) is added. Stirring is continued for an additional 120 min. The resulting solution is treated with sodium acetate (296 g) and the sodium chloride that forms is filtered out. The solution is then dried until a homogenous powder forms. Yield is 1306 g of powder. Copper content is 9.8%.

$p/(r+p)=0.3\pm0.1$
$m=2$
$n=1.33$
The ratio of copper (gmol)/ascorbic acid (gmol)=4
The ratio of copper (gmol)/rutin (gmol)=2

EXAMPLE 12

To an alcohol solution (95% ethanol) of divalent copper containing 1 gmol of copper (2) in the form of copper chloride (135 g) is added 0.5 gmol of ascorbic acid (90 g), and the mixture is stirred while boiling with reflux for 90 min. With constant stirring, 1 gmol of rutin (650 g) is added. Stirring is continued for an additional 120 min. The resulting solution is treated with sodium acetate (148 g) and the sodium chloride that forms is filtered out. The solution is then dried until a homogenous powder forms. Yield is 1023 g of powder. Copper content is 6.3%.

$p/(r+p)=0.15\pm0.1$
$m=1$
$n=0.7$
The ratio of copper (gmol)/ascorbic acid (gmol)=2
The ratio of copper (gmol)/rutin (gmol)=2

EXAMPLE 13

To an alcohol solution (95% ethanol) of divalent copper containing 3 gmol of copper (2) in the form of copper chloride (405 g) is added 0.5 gmol of ascorbic acid (90 g), and the mixture is stirred while boiling with reflux for 90 min. With constant stirring, 1 gmol of rutin (650 g) is added. Stirring is continued for an additional 120 min. The resulting solution is treated with sodium acetate (444 g) and the sodium chloride that forms is filtered out. The solution is then dried until a homogenous powder forms. Yield is 1589 g of powder. Copper content is 12.1%.

$p/(r+p)=0.5\pm0.1$
$m=3$
$n=2$
The ratio of copper (gmol)/ascorbic acid (gmol)=6
The ratio of copper (gmol)/rutin (gmol)=3

EXAMPLE 14

To an alcohol solution (95% ethanol) of divalent zinc containing 2 gmol of zinc (2) in the form of zinc chloride (272 g) is added 0.5 gmol of ascorbic acid (90 g), and the mixture is stirred while boiling with reflux for 90 min. With constant stirring, 1 gmol of rutin (650 g) is added. Stirring is continued for an additional 120 min. The resulting solution is treated with sodium acetate (296 g) and the sodium chloride that is formed is filtered out. The solution is then dried until a homogenous powder forms. Yield is 1308 g of powder. Zinc content is 9.9%.

$p/(r+p)=0\pm0.05$
$m=2$
$n=1.33$
The ratio of zinc (gmol)/ascorbic acid (gmol)=4
The ratio of zinc (gmol)/rutin (gmol)=2

EXAMPLE 15

To an alcohol solution (95% ethanol) of divalent zinc containing 1 gmol of zinc (2) in the form of zinc chloride (136 g) is added 0.5 gmol of ascorbic acid (90 g), and the mixture is stirred while boiling with reflux for 90 min. With constant stirring, 1 gmol of rutin (650 g) is added. Stirring is continued for an additional 120 min. The resulting solution is treated with sodium acetate (148 g) and the sodium chloride that forms is filtered out. The solution is then dried until a homogenous powder forms. Yield is 1024 g of powder. Zinc content is 6.3%.

$p/(r+p)=0.0\pm0.05$
$m=1$
$n=0.7$
The ratio of zinc (gmol)/ascorbic acid (gmol)=2
The ratio of zinc (gmol)/rutin (gmol)=2

EXAMPLE 16

To an alcohol solution (95% ethanol) of divalent zinc containing 3 gmol of zinc (2) in the form of zinc chloride (408 g) is added 0.5 gmol of ascorbic acid (90 g), and the mixture is stirred while boiling with reflux for 90 min. With constant stirring, 1 gmol of rutin (650 g) is added. Stirring is continued for an additional 120 min. The resulting solution is treated with sodium acetate (444 g) and the sodium chloride that forms is filtered out. The solution is then dried until a homogenous powder forms. Yield is 1592 g of powder. Zinc content is 12.1%.

$p/(r+p)=0.0\pm0.05$
$m=3$
$n=2$

The ratio of zinc (gmol)/ascorbic acid (gmol)=6
The ratio of zinc (gmol)/rutin (gmol)=3

EXAMPLE 17

To an alcohol solution (95% ethanol) of divalent manganese containing 2 gmol of manganese (2) in the form of manganese chloride (252 g) is added 0.5 gmol of ascorbic acid (90 g), and the mixture is stirred while boiling with reflux for 90 min. With constant stirring, 1 gmol of rutin (650 g) is added. Stirring is continued for an additional 120 min. The resulting solution is treated with sodium acetate (296 g) and the sodium chloride that forms is filtered out. The solution is then dried until a homogenous powder forms. Yield is 1288 g of powder. Manganese content is 8.5%.
p/(r+p)=0±0.05
m=2
n=1.33
The ratio of manganese (gmol)/ascorbic acid (gmol) =4
The ratio of manganese (gmol)/rutin (gmol)=2

EXAMPLE 18

To an alcohol solution (95% ethanol) of divalent manganese containing 1 gmol of manganese (2) in the form of manganese chloride (126 g) is added 0.5 gmol of ascorbic acid (90 g), and the mixture is stirred while boiling with reflux for 90 min. With constant stirring, 1 gmol of rutin (650 g) is added. Stirring is continued for an additional 120 min. The resulting solution is treated with sodium acetate (148 g) and the sodium chloride that forms is filtered out. The solution is then dried until a homogenous powder forms. Yield is 1014 g of powder. Manganese content is 5.4%.
p/(r+p)=0.0±0.05
m=1
n=0.7
The ratio of manganese (gmol)/ascorbic acid (gmol) =2
The ratio of manganese (gmol)/rutin (gmol)=2

EXAMPLE 19

To an alcohol solution (95% ethanol) of divalent manganese containing 3 gmol of manganese (2) in the form of manganese chloride (378 g) is added 0.5 gmol of ascorbic acid (90 g), and the mixture is stirred while boiling with reflux for 90 min. With constant stirring, 1 gmol of rutin (650 g) is added. Stirring is continued for an additional 120 min. The resulting solution is treated with sodium acetate (444 g) and the sodium chloride that forms is filtered out. The solution is then dried until a homogenous powder forms. Yield is 1562 g of powder. Manganese content is 10.6%.
p/(r+p)=0.0±0.05
m=3
n=2
The ratio of manganese (gmol)/ascorbic acid (gmol) =6
The ratio of manganese (gmol)/rutin (gmol)=3

Granules are prepared using the above described compounds with polyvinylpyrrolidone (PVP) and eudragit (acrylic polymers) are auxiliary agents. The process is conducted using standard granule-producing equipment i.e., a spray drier, a fluidized-bed drier-granulator, a coating drum, etc.

The resulting granules are used in production of tablets or capsules, using microcrystalline cellulose, calcium stearate, and talc as auxiliary agents.

Water-alcohol solutions are also prepared using the described complexes.

EXAMPLE 20

100 g of complex obtained in Example 1 is placed in a preheated (50° C.) coating drum. With constant rotation, the complex is sprayed with 60 mL of 5 wt % aqueous PVP solution. The drum is aerated with air heated to 60° C., at an intensity not exceeding the entrainment of matter from the drum. Then, with constant rotation, 30 mL of 30% aqueous eudragit (acrylic polymer) suspension are sprayed into the drum; the amount of suspension required for full coating is equal to 30 wt % of the amount of complex. After the final drying of the granules, the coating drum is unloaded. The weight of the produced granules is 112 g; and the iron content is 10%.

Tables 1 and 2 below give examples of granules obtained in Examples 1-7 and 10-19.

TABLE 1

| Example # of the prepared granulate | Product used derived from example # | Temperature of the coating drum ° C. | Temperature of the air circulation ° C. | Concentration of the suspension of eudragit % | Volume of the suspension eudragit (mL) | Concentration of the PVP solution % | Volume of PVP (mL) |
|---|---|---|---|---|---|---|---|
| 20 | 1 | 40 | 60 | 30 | 30 | 5 | 100 |
| 21 | 2 | 50 | 60 | 20 | 20 | 10 | 20 |
| 22 | 3 | 40 | 70 | 10 | 30 | 5 | 20 |
| 23 | 4 | 40 | 40 | 30 | 40 | 0 | 0 |
| 24 | 5 | 50 | 60 | 20 | 60 | 0 | 0 |
| 25 | 6 | 50 | 60 | 30 | 35 | 0 | 0 |
| 26 | 7 | 50 | 60 | 30 | 25 | 5 | 40 |
| 27 | 10 | 40 | 60 | 0 | 0 | 5 | 100 |
| 28 | 11 | 50 | 60 | 20 | 20 | 10 | 20 |
| 29 | 12 | 40 | 70 | 10 | 30 | 5 | 20 |
| 30 | 13 | 40 | 40 | 30 | 40 | 0 | 0 |
| 31 | 14 | 50 | 60 | 0 | 0 | 5 | 100 |
| 32 | 15 | 40 | 60 | 20 | 20 | 10 | 20 |
| 33 | 16 | 50 | 60 | 10 | 30 | 5 | 20 |
| 34 | 17 | 40 | 70 | 30 | 40 | 0 | 0 |
| 35 | 18 | 40 | 40 | 0 | 0 | 5 | 100 |
| 36 | 19 | 50 | 60 | 20 | 20 | 10 | 20 |

Table 2 contains the content of the derived granules.

TABLE 2

| Example # of the prepared granulate | Product used derived from example # | Amount suspension eudragit (g) | Concentration of eudragit in the granulate % | Amount of PVP (g) | Concentration of PVP in the granulate % | Iron concentration % | Copper concentration % | Zinc concentration % | Manganese concentration % |
|---|---|---|---|---|---|---|---|---|---|
| 20 | 1 | 9 | 7.9 | 5 | 4.4 | 10 | | | |
| 21 | 2 | 4 | 3.8 | 2 | 1.9 | 5.6 | | | |
| 22 | 3 | 3 | 2.9 | 1 | 1.0 | 8.4 | | | |
| 23 | 4 | 12 | 10.7 | 0 | 0 | 10 | | | |
| 24 | 5 | 12 | 10.7 | 0 | 0 | 5.9 | | | |
| 25 | 6 | 10.5 | 9.5 | 0 | 0 | 5.9 | | | |
| 26 | 7 | 7 | 6.4 | 2 | 1.8 | 7.9 | | | |
| 27 | 10 | 0 | 0 | 5 | 4.8 | 8.0 | | | |
| 28 | 11 | 4 | 3.8 | 2 | 1.9 | | 9.2 | | |
| 29 | 12 | 3 | 2.9 | 1 | 0.9 | | 6.1 | | |
| 30 | 13 | 12 | | 0 | 0 | | 10.8 | | |
| 31 | 14 | 0 | 0 | 5 | 4.8 | | | | 9.4 |
| 32 | 15 | 4 | 3.8 | 2 | 1.9 | | | | 6.0 |
| 33 | 16 | 3 | 2.9 | 1 | 0.9 | | | | 11.6 |
| 34 | 17 | 12 | 10.7 | 0 | 0 | | | 7.6 | |
| 35 | 18 | 0 | 0 | 5 | 4.8 | | | 5.1 | |
| 36 | 19 | 4 | 3.8 | 2 | 1.9 | | | 10.0 | |

Preparation of Tablets or Capsules

EXAMPLE 37

100 g of granulate obtained as in Example 20 are placed into a planetary mixer, and 2 g calcium stearate, 2 g talc, and 96 g microcrystalline cellulose are added. Total weight of additional agents is 100 g. Mix for 60 min. The mixture is then pressed into 100 mg tablets or is encapsulated in gelatin capsules (50% additional components). The content of iron in a tablet/capsule is 5 mg.

EXAMPLE 38

187 g of granular compound derived from Example 21 are placed into a planetary mixer, and 2 g calcium stearate, 2 g talc, and 19 g microcrystalline cellulose are added. The total weight of additional components is 23 g (11% additional components). After mixing for 60 min, the mixture is then pressed into 100 mg pills or encapsulated in hard gelatin capsules.

The content of iron in a pill/capsule is 5 mg.

Examples 39-42 are completed in an analogous manner and are summarized in Table 3.

Preparation of Water-Alcohol Solutions

EXAMPLE 43

20 g of complex obtained as in Example 6 are dissolved in 1000 mL water-alcohol solution (30% ethanol), which is then filtered through a 0.2 micron filter. The filtered solution is then placed into 5 mL ampules. The iron content in 1 ampule is 6.5 mg.

EXAMPLE 44

20 g of complex obtained as in Example 6 are dissolved in 1000 mL water-alcohol solution (30% ethanol), which is then filtered through a 0.2 micron filter. The filtered solution is then placed into 15 mL vials. The iron content in 1 vial is 20 mg.

Evaluation of the Effect of the Complexes in Capsule or Tablet Form on the Level of Oxygenation of Healthy Muscle Tissue in Animals The experiment was conducted on hybrid mice F1(CBAxC57bl/6j), males weighing 25-27 g. The mixture as in Example 38 was injected directly into the stomach of the animal with a syringe once in a dose of 200 mg/kg. Two hours

TABLE 3

| Example # | Amount of granulate (g) | Granulate made following example # | Amount of microcrystalline cellulose (g) | Iron content (mg) in 100 mg pill | Copper content (mg) in 100 mg pill | Zinc content (mg) in 100 mg pill | Manganese content (mg) in 100 mg pill |
|---|---|---|---|---|---|---|---|
| 37 | 100 | 20 | 96 | 5 | | | |
| 38 | 187 | 21 | 19 | 5 | | | |
| 39 | 100 | 26 | 54 | 5 | | | |
| 40 | 10 | 28 | 170 | | 0.5 | | |
| 41 | 50 | 31 | 63 | | | 4.0 | |
| 42 | 20 | 34 | 128 | | | | 1.0 | after injection, an increase from 27±10 mm Hg to 44±15 mm Hg (~40% increase) in partial pressure of oxygen in healthy mouse muscle tissue was observed. The determination of oxygen partial pressure in healthy mouse muscle tissue involved measuring the decrease of phosphorescence of a Palladium (II) meso-tetraphenyl-tetrabenzoporphyrin (PdPh$_4$TBP) sensor in the presence of oxygen. PdPh$_4$TBP was excited using impulses having a duration of 20 microseconds from a helium-neon (He—Ne) laser (wave length 633 nm, potential of 50 millivolt). The kinetics of the decrease in phosphorescence is dependent on the partial pressure of oxygen in the biological environment surrounding the sensor. To register that data a photomultiplier is used.

RADIOPROTECTIVE PROPERTIES

The radioprotective properties were tested on hybrid mice C57/Black6 weighing 18-22 g. Two groups of 10 mice were exposed to 8 Gy of gamma radiation each. Four hours prior to irradiation, the test group received orally 10 mg of the mixture of Example 37. At the end of the observation period, the control group lost 5 animals, and the test group lost 2 animals.

CORRECTION OF THE BIOLOGICAL AGE OF A HUMAN

Studies were conducted to test the effect of the described complexes on decreasing the biological age of humans. The following method was used in determining the biological age of humans. After a night of rest, buccal epithelial cells were collected and subjected to microelectrophoresis. The ratio of electronegative nuclei to the total amount of cells studied is measured. This ratio is then compared to a preestablished standard for a given biological age (USSR 1169614, A61B 10/00, 1981). The human biological age was determined from the table of standard values of the ENN (electronegativity of cell nuclei).

Group 1: Women, actual age 40-50 years. Average biological age prior to treatment is 55 years. Taking 1 capsule of the mixture of Example 38 (100 mg) every 2 days, after 40 days, the average biological age was 38 years.

Group 2: Women, actual age 40-50 years. Average biological age prior to treatment is 58 years. Taking 1 capsule of the mixture of Example 38 (100 mg) daily, after 40 days, the average biological age was 44 years.

Group 3: Men, actual age 45-50 years. Average biological age prior to treatment is 61 years. Taking 1 capsule of the mixture of Example 38 (100 mg) daily, after 40 days, the average biological age was 42 years.

Parkinson's Disease

A group of 10 volunteers (initial stages of the disease) was randomly divided in half.

The test group in conjunction with standard treatment (Levodopa, bromocryptin, MAO inhibitors) was given the mixture (100 mg, once daily) as in Example 39.

The observation was conducted over a 3-month period; the progression of the symptoms listed in Table 6 was evaluated considering the initial symptoms as 100%. Table 4 gives initial symptoms (before starting the course of treatment with the preparation prepared following Example 39) and final symptoms of the illness.

TABLE 4

| Symptom | Test Group | Control Group | Ratio |
|---|---|---|---|
| Involuntary tremor | 100/100; 100/101; 100/100; 100/100; 100/101 | 100/103; 100/102; 100/105; 100/101; 100/104 | 100.4/103 |
| Muscle rigidity | 100/101; 100/101; 100/100; 100/100; 100/101 | 100/103; 100/103; 100/104; 100/101; 100/103 | 100.6/102.9 |
| Bradykinesia (slow unsteady gait) | 100/100; 100/101; 100/100; 100/101; 100/101 | 100/103; 100/102; 100/102; 100/104; 100/104 | 100.6/103 |
| Bradyphrenia (Slowed thought, speed, emotional processes) | 100/101; 100/101; 100/100; 100/100; 100/101 | 100/103; 100/102; 100/105; 100/102; 100/101 | 100.6/102.6 |
| Postural instability (loss of physical coordination) | 100/100; 100/101; 100/101; 100/100; 100/101 | 100/103; 100/101; 100/103; 100/102; 100/104 | 100.6/102.6 |

The data shows a tendency toward a reduction of disease symptoms.

ALZHEIMER'S DISEASE

A group of 10 volunteers (initial stages of the disease) was randomly divided in half.

The test group, along with standard treatment (Vinpocetine (Cavinton), dihydroergotamine mesylate, amantadine bifemelane, acetyl-L-carnitine, indolaksozin, paracetam) was given a mixture made as in Example 39 (100 mg, once daily).

The observation was conducted over a 3-month period; the progression of the symptoms listed in Table 5 was evaluated considering the initial symptoms as 100%. Table 5 gives initial symptoms (before starting the course of treatment with the mixture prepared following Example 39) and final symptoms of the illness.

TABLE 5

| Symptom | Test Group | Control Group | Ratio |
|---|---|---|---|
| Agnosia (loss of ability to recognize objects) | 100/100; 100/101; 100/100; 100/100; 100/101 | 100/103; 100/101; 100/103; 100/102; 100/104 | 100.4/102.6 |
| Inability to orient in space and time | 100/101; 100/101; 100/100; 100/100; 100/101 | 100/103; 100/103; 100/104; 100/101; 100/103 | 100.6/102.9 |
| Bradykinesia (slow unsteady gait) | 100/100; 100/101; 100/100; 100/101; 100/101 | 100/103; 100/102; 100/102; 100/104; 100/104 | 100.6/103 |
| Bradyphrenia (Slowed thought, speed, emotional processes) | 100/101; 100/101; 100/100; 100/100; 100/101 | 100/103; 100/102; 100/105; 100/102; 100/101 | 100.6/102.6 |

TABLE 5-continued

| Symptom | Test Group | Control Group | Ratio |
|---|---|---|---|
| Loss intellectual-mnestic functions (memory, attention, logic, communication) | 100/100; 100/101; 100/101; 100/100; 100/101 | 100/103; 100/102; 100/105; 100/101; 100/104 | 100.6/103 |

The data shows a tendency of toward a reduction of the development of symptoms.

What is claimed is:

1. An antioxidant composition for the treatment or prophylaxis of an illness associated with oxidative stress, the composition comprising:
a chemical reaction product comprising a complex comprising a metal, rutin and at least one of ascorbic acid and dehydroascorbic acid, the complex represented by the general formula (I):

$$Me_mRu(AA)_r(DGAA)_p\text{-}X_n \qquad (I), \text{wherein}$$

Me is a cation of a metal selected from the group consisting of iron, copper, zinc and manganese;
Ru is rutin;
AA is ascorbic acid;
DGAA is dehydroascorbic acid;
X is selected from the group consisting of $SO_4^{-2}$, $CH_3C(O)O^-$ and $^-OOC\text{—}CH_2\text{—}C(OH)(COO^-)\text{—}CH_2\text{—}COO^-$,
m is a value from 1.0 to 3;
n is a value from 0.7 to 9; and
p/(r+p) is a value from 0 to 1, and each of p and r is a value of 0 to 0.5, provided that when p=0 then r is not equal to 0, and when r=0 then p is not equal to 0.

2. The antioxidant composition of claim 1, wherein the metal is iron, m is the number of atoms of iron with degree of oxidation 3 and has a value from 1.5 to 3.

3. The antioxidant composition of claim 1, wherein the metal is copper, and n is a value from 0.7 to 6.

4. The antioxidant composition of claim 1, wherein the metal is zinc, and n is a value from 0.7 to 6.

5. The antioxidant composition of claim 1, wherein the metal is manganese, and n is a value from 0.7 to 6.

6. The antioxidant composition of claim 1 in a granulate form.

7. The antioxidant composition of claim 6 which further comprises a further component selected from the group consisting of polyvinyl pyrrolidone, an acrylic polymer and mixtures thereof.

8. The antioxidant composition of claim 7, wherein the polyvinyl pyrrolidone is present in an amount between 0 and 5.0% by weight of the composition, and the acrylic polymer is present in an amount between 0 and 11% by weight of the composition.

9. The antioxidant composition of claim 1 in a dosage form selected from the group consisting of a tablet and a capsule.

10. The antioxidant composition of claim 9, wherein the dosage form further comprises an effective amount of a supplemental component.

11. The antioxidant composition of claim 10, wherein the supplemental component is selected from the group consisting of microcrystalline cellulose, stearate salt of calcium, stearate salt of magnesium, talc and mixtures thereof.

12. The antioxidant composition of claim 10, wherein the supplemental component is present in a total of 15 to 50% by weight of the dosage form.

13. The antioxidant composition of claim 1 in the form of a solution.

14. The antioxidant composition of claim 13, wherein the solution is an aqueous solution.

15. The antioxidant composition of claim 13, wherein the solution is an aqueous alcohol solution.

16. A method of making an antioxidant composition comprising a complex comprising a metal, rutin and at least one of ascorbic acid and dehydroascorbic acid, the complex represented by the general formula (I):

$$Me_mRu(AA)_r(DGAA)_p\text{-}X_n \qquad (I), \text{wherein}$$

Me is a cation of a metal selected from the group consisting of iron, copper, zinc and manganese;
Ru is rutin;
AA is ascorbic acid;
DGAA is dehydroascorbic acid;
X is selected from the group consisting of $SO_4^{-2}$, $CH_3C(O)O^-$ and $^-OOC\text{—}CH_2\text{—}C(OH)(COO^-)\text{—}CH_2\text{—}COO^-$,
m is a value from 1.0 to 3;
n is a value from 0.7 to 9; and
p/(r+p) is a value from 0 to 1 and each of p and r is a value of 0 to 0.5, provided that when p=0 then r is not equal to 0, and when r=0 then p is not equal to 0, the method comprising:
reacting ascorbic acid with a salt of a metal selected from the group consisting of iron, copper, zinc and manganese in solution to form a product; and,
contacting the product with rutin at temperatures between room temperature and the boiling point of the solution to produce a rutin-containing product.

17. The method of claim 16, wherein the salt of the metal is selected from the group consisting of chloride, sulfate, acetate and citrate.

18. The method of claim 16, wherein the solution contains an alcohol.

19. The method of claim 16, wherein the salt of the metal is a strong acid salt, and the method further comprises treating the rutin-containing product with an alkali metal salt of a weak acid.

* * * * *